United States Patent
Caruso et al.

(10) Patent No.: US 7,045,146 B2
(45) Date of Patent: *May 16, 2006

(54) TEMPLATING OF SOLID PARTICLES BY POLYMER MULTILAYERS

(75) Inventors: Frank Caruso, Golm (DE); Dieter Trau, Kowloon (HK); Helmuth Möhwald, Bingen (DE); Reinhard Renneberg, Kowloon (HK)

(73) Assignee: Max-Planck-Gesellschaft zur Forderung der Wissenschaften e.V., Munich (DE)

(*) Notice: Subject to any disclaimer, the term of this patent is extended or adjusted under 35 U.S.C. 154(b) by 440 days.

This patent is subject to a terminal disclaimer.

(21) Appl. No.: 10/148,890

(22) PCT Filed: Jan. 12, 2001

(86) PCT No.: PCT/EP01/00329

§ 371 (c)(1),
(2), (4) Date: Jun. 17, 2002

(87) PCT Pub. No.: WO01/51196

PCT Pub. Date: Jul. 19, 2001

(65) Prior Publication Data

US 2002/0187197 A1    Dec. 12, 2002

(30) Foreign Application Priority Data

Jan. 13, 2000   (DE) .............................. 100 01 172
May 29, 2000   (EP) .............................. 00111523

(51) Int. Cl.
  A61K 9/48    (2006.01)
  A61K 9/66    (2006.01)
  A61K 9/64    (2006.01)
  A61K 9/14    (2006.01)
  A61K 9/16    (2006.01)

(52) U.S. Cl. ............ 424/463; 424/450; 424/451; 424/455; 424/460; 424/461; 424/462; 424/489; 424/490; 424/494; 424/496; 424/497

(58) Field of Classification Search ............ 424/451, 424/455, 450, 460, 461, 462, 463, 489, 490, 424/494, 496, 497
See application file for complete search history.

(56) References Cited

U.S. PATENT DOCUMENTS 6,013,284 A       1/2000    Samain et al.
6,699,501 B1 *    3/2004    Sukhobukov et al. ....... 424/463
6,833,192 B1 *    12/2004   Caruso et al. .............. 428/403

FOREIGN PATENT DOCUMENTS

DE    198 12 083    9/1999
DE    199 07 552    8/2000
WO    99 47252      9/1999
WO    99 47253      9/1999
WO    00 03797      1/2000

* cited by examiner

Primary Examiner—Thurman K. Page
Assistant Examiner—Humera N. Sheikh
(74) Attorney, Agent, or Firm—Rothwell, Figg, Ernst & Manbeck, P.C.

(57) ABSTRACT

Process for encapsulation of an uncharged crystalline solid particle include treating the crystalline solid particle material with amphiphilic substances and subsequently coating the material with a layer of charged polyelectrolyte or coating the material with a multilayer comprising alternating layers of oppositely charged polyelectrolytes.

54 Claims, 5 Drawing Sheets

TEMPLATING OF SOLID PARTICLES BY POLYMER MULTILAYERS

Figure 1:
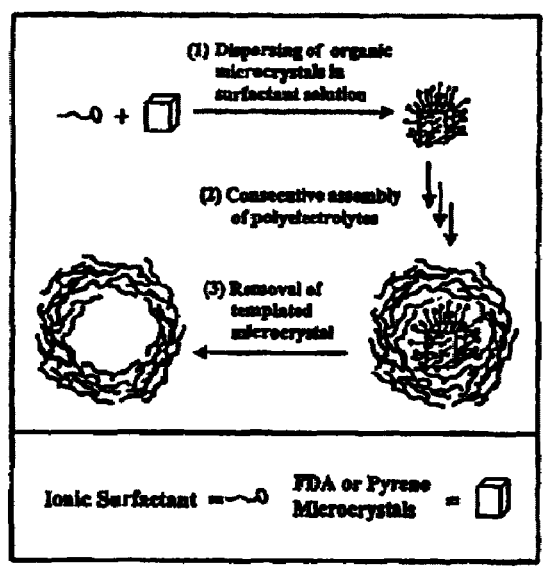

The invention is directed to (i) the encapsulation of uncharged organic substances in polymeric capsules by using a multi-step strategy that involves the introduction of charge to the surface of the microcrystals with an amphiphilic substance, followed by consecutively depositing polyelectrolytes of opposite charge to assemble a multilayered shell of polymeric material around the microcrystal template, and (ii) the formation of polymer multilayer cages derived from the coated crystals by facile removal of the crystalline template.

In recent years, microcapsules have received considerable attention because of their technological importance in the fields of medicine, pharmaceutics, agriculture and cosmetics.[1-7] The vast majority of applications are associated with the controlled release of encapsulated active ingredients (e.g. drugs, vaccines, antibodies, hormones, pesticides and fragrances) under well-defined conditions. Despite the array of encapsulation technologies available, including those based on liposomes, microparticles and microemulsions, there has been an intense interest in strategies to encapsulate and deliver water-insoluble pharmaceutical drugs in stable and aqueous forms.[8,9] Methods to achieve this have commonly included the incorporation of such drugs into micelles and microspheres, emulsification of the drug with oils, the use of concentrated solutions of water-soluble polymers, as well as solubilization or suspending the drug with non-ionic detergents. An alternative and recent approach has been to coat water-insoluble crystalline drugs with a membrane lipid, thus allowing dispersion of the crystal in an aqueous medium.[9] This represents an elegant method to prepare injectable forms of water-insoluble substances. The advantages of this process are the significantly higher concentrations (up to 40% w/v) of the injectable drug afforded (compared with other methods), and the stability of the coated dispersion.

The coupling of self-assembly and colloidal templating provides an elegant and versatile means to encapsulate a variety of functional materials including biological macromolecules and to create core-shell structures for potential use in the fields of medicine, pharmaceutics, catalysis and separations.[10-18] The method entails coating colloidal particles dispersed in aqueous media by the nanoscale electrostatic self-assembly of charged polymeric materials. This strategy exploits the fact that the colloidal entities, which serve as the templates, have an inherent surface charge, thus rendering them water dispersible and providing the necessary charge essential for adsorption of subsequent layers and polyelectrolyte multilayer encapsulation. Recently, this approach has been employed to entrap proteins[18] and construct new classes of composite colloids.[11-17] The colloids employed have ranged from charged polymer latices[11-17] to biological templates, e.g. cells[10] and protein crystals[18].

Solid crystalline organic compounds are an important class of materials that are widely employed in pharmaceutics as drugs. The controlled coating of such compounds is of widespread interest.[19] However, many crystalline materials that are of significance in medicine, for example crystals composed of low molecular weight drugs, are uncharged and have a low solubility in water. For such drugs, their encapsulation and application in an aqueous medium often represents a substantial problem.

An object of the invention was therefore to provide a method for the encapsulation of uncharged materials.

The problem underlying the invention is solved by a process for the encapsulation of an uncharged solid particle material comprising (a) treating the solid particle material with an amphiphilic substance and
(b) subsequently coating the solid material with a layer of charged polyelectrolyte or with a multilayer comprising alternating layers of oppositely charged polyelectrolytes.

The encapsulation of materials by using colloidal templating was extended to uncharged solid templates, thereby presenting an alternative and advantageous strategy to other encapsulation methods.

With the process according to the invention it is surprisingly possible to encapsulate uncharged solid particle materials, in particular, organic crystalline templates that are largely water insoluble and/or hydrophobic. Thus, the method is applicable to a wide variety of substances and in particular to substances which are of high pharmaceutical interest.

In the first step of the process the uncharged solid particle materials are treated with an amphiphilic substance, which imparts charge on the surface of the particle materials. Then in the second step the material coated with amphiphilic substance is coated again with a polyelectrolyte which is oppositely charged to the surface of the coated particle materials. For the formation of multilayers the material is subsequently treated with oppositely charged polyelectrolytes, i.e. alternately with cationic and anionic polyelectrolytes. Polymer layers self-assemble onto the pre-charged solid templates by means of electrostatic layer-by-layer deposition, thus forming a multilayered polymeric shell around the solid cores.

Due to the semi-permeable nature of the polymer multilayer shell, it is further possible to remove the templated solid core, e.g. by exposure to a mild organic solvent. The process according to the invention thus provides a novel and facile pathway to the fabrication of polymer multilayered microcapsules as well as superior strategy for the encapsulation of hydrophobic compounds such as drugs.

The limited potential of medical drugs is associated with their low solubility in aqueous solutions. Most drugs are solid crystalline substances, containing non-polar aromatic groups (amphetamines) and/or heterocyclic groups (1,4-benzodiazepime), or condensed aromatic or alicyclic groups (isoprenoids: steroid, vitamin A, vitamin E) and mostly one or more polar functional group (e.g. amine, hydroxy, carboxy, phenolic, aldehyde, ketone). Their formulation is a key factor for allowing their use in the human body.

The here-described method provides a strategy for:

A) The encapsulation of water-insoluble, uncharged solid particle material, e.g. drug crystals or/and amorphous (glassy) materials;
B) The production of hollow polymer capsules.

A) The starting material is the solid substance itself. Due to the uncharged and hydrophobic character of these materials, they cannot be directly coated with polyelectrolytes. The described method makes it possible to introduce a surface charge to the crystal by treatment with a charged amphiphilic species (e.g. ionic surfactants). This leads to the formation of a stable suspension of the coated substance in water. Typical surface potentials after treatment with an amphiphile (e.g. sodium dodecyl sulfate, SDS) are between $-50$ and $-70$ mV, indicating a suspension of surfactant-charged crystals of high stability. The charged crystals are then suitable templates for coating with polyelectrolytes.

One advantage of this innovation is the possibility to create a drug release system with a constant release rate over a long time period. This is possible because of the solid phase in the interior of the capsule. After the encapsulated solid material is applied in a liquid such as a buffer or body fluid, a two-phase system will be established by the crystal itself and a saturated solution of the crystal material in the interior of the capsule. By contacting the capsules prepared according to the invention, which consist of an encapsulated solid material, with a liquid such as water, the liquid penetrates into the capsules. Thereby the wall of the capsule swells to some degree and within the capsule a small portion of the solid material is solubilized until saturation of the penetrated liquid is reached. As release of the material occurs, the amount of substance released from the capsule is continuously replenished by further solubilization of solid material within the capsule. Therefore the concentration of the substance in the liquid within the capsule remains almost constant. Consequently, a constant release of the substance over a long period of time can be achieved.

The process of the invention is particularly suitable to prepare release systems, which release a small amount of active substance constantly over an extended period of time. Such a system advantageously comprises a high diffusion barrier across the wall of the capsule, which results in a small amount of released substance with respect to the amount of substance which can be supplemented in the same period of time by solubilization of solid material within the capsule. Such release systems are particularly useful in hormone therapy wherein the constant release of small amounts of active substance is required.

The release rate of a substance is a function of the difference in its concentration in and outside of the capsule. The described approach provides a method to keep this concentration gradient constant as long as the solid material is not dissolved completely. This would lead to a constant release rate of the substance over a long time period. This method provides an advantage over other release systems that use a dissolved substance in a capsule or liposome. The concentration of the dissolved substance in those capsules or liposomes is decreased from the first moment of the release, and the release rate is not constant.

B) The method shows also the possibility for the production of hollow polymer capsules. Until now the template removal process has employed harsh conditions (e.g. pH<1.6, pH>11), in order to decompose the polymeric-template and to remove it out of the capsule. Using these harsh procedures the capsule itself in many cases is damaged and changed in its properties. This problem can be overcome by using a non polymer-template like a crystallized, hydrophobic low molecular weight substance (as explained above). This substance can be easily removed after encapsulation by treatment with a mild organic solvent (e.g. ethanol). The substance is dissolved and readily penetrates through the polymer multilayers. The shells can then be pelleted by centrifugation and resuspended in an aqueous solution.

According to the invention a solid uncharged material is encapsulated in two steps. First, the solid uncharged material is treated with an amphiphilic substance. This treatment preferably results in an aqueous dispersion of the solid material. The amphiphilic substance is arranged on the surface of the solid material, rendering the material susceptible to the subsequent coating with a charged polyelectrolyte. The uncharged material used in the present invention is preferably a material which has no charges and also has no ionizable groups. It is also possible, however, to use an uncharged material having ionizable groups, whereby this material can be used under conditions, under which the ionizable groups are not ionized. The encapsulation process according to the invention is therefore applicable to a wide range of materials, whose encapsulation in a solid form has previously not been possible or possible only under very specific conditions. In a second step, the solid particle material having the amphiphilic substance assembled on its surface is coated with a layer of a charged polyelectrolyte or with a multilayer comprising alternating layers of oppositely charged polyelectrolytes. The coating of the charged polyelectrolyte onto the surface is made possible by the amphiphilic substance. By successive treatment with oppositely charged polyelectrolytes multilayer coatings can be prepared. Preferably, capsules are prepared having at least two, more preferably at least three, still more preferably at least five and most preferably at least eight layers of polyelectrolytes having alternating charge. However, it is also possible to prepare thicker shells having e.g. up to 100 or more polyelectrolyte layers, preferably up to 50 and most preferably up to 20 layers. The assembly of thicker shells has the effect of smoothing out the outer surface and at the same time reducing the porosity of the shells.

By the number of polyelectrolyte layers, by selecting the amphiphilic substance and the polyelectrolytes used and by the conditions during coating with the amphiphilic substance the porosity of the capsules can be influenced. In this way, pore sizes specifically designed for the respective application can be obtained. Monomeric detergents such as SDS, for example, lead to small pores, whereas by polymeric detergents such as PSS larger pores are obtained in the capsule wall. The conditions applied when charging the solid material with the amphiphilic substance can influence pore size, e.g., if polymeric detergents are used, by determining the shape of the polymeric detergent. Ionic strength and pH value, for example, can determine whether the polymeric detergent is present in elongated or coiled form. For example, pores having a diameter of about 20 nm to >100 nm can be obtained in the capsule walls, if an amphiphilic polyelectrolyte is used as the amphiphilic substance. However, if an ionic surfactant is used as the amphiphilic substance, smaller pore sizes of less than about 5 to 10 nm can be obtained. The porosity of the capsule can be decreased by a further cross-linking step, in which a reagent is used to introduce inter- and intra-crosslinks of polyelectrolytes in the shells.

The thickness of the capsule shell preferably is about 2 to 100 nm, more preferably 5 to 50 nm. The size of the capsules themselves preferably is <50 µm, in particular, <20 µm and more preferably <15 µm; however, it is also possible to prepare larger capsules. The minimum size of the capsules preferably is at least 10 nm, more preferably at least 50 nm. The capsule size basically depends on the size of the solid material used.

The method of the invention is especially suitable for uncharged solid material which has a low solubility in water or is water-insoluble or not dispersible in water. The encapsulation of such materials was difficult in the prior art and can now be managed easily according to the invention.

The uncharged solid material used as core for the encapsulation can be an organic material, a biomaterial or/and an inorganic material. Organic materials, in particular, solid materials from low-molecular weight organic compounds can be encapsulated especially favorably. According to the invention, encapsulation of uncharged solid organic crystalline templates that are largely water-insoluble is possible. Suitable materials which can be encapsulated according to the method of the invention, for example, are drugs, vitamins, nutrients, hormones, growth factors, pesticides, antibiotics and preservatives. According to the invention it is not necessary thereby for the materials to have a charged or ionizable group.

The shape of the capsules largely depends on the shape of the solid material used. Suitably, the solid material is employed as crystalline material, e.g. in the form of single crystals, as amorphous or lyophilized materials, spray-dried materials and/or milled materials. It is particularly preferred to use microcrystals of the uncharged compounds to be encapsulated. Basically, any uncharged solid material can be encapsulated, e.g. a synthetic material, a material isolated from natural sources or a chemically modified isolated material.

As amphiphilic substance according to the invention any substance can be used which has ionic hydrophilic and hydrophobic groups. It is important that the amphiphilic substance has at least one electrically charged group to provide the solid material with electrical charges. Therefore, the amphiphilic substance used also can be referred to as ionic amphiphilic substance or ionic detergent. Preferably, ionic surfactants, phospholipids and/or amphiphilic polyelectrolytes are used. Amphiphilic polyelectrolytes, for example, are polyelectrolytes comprising a charged group as hydrophilic group and a hydrophobic group, e.g. aromatic groups. It is preferred to use a cationic or/and anionic surfactant. Examples of suitable cationic surfactants are quaternary ammonium salts ($R_4N^+X^-$), especially didodecyldimethylammonium bromide (DDDAB), alkyltrimethylammonium bromides, especially dodecyltrimethylammonium bromide or palmityl trimethylammonium bromide or N-alkylpyridinium salts or tertiary amines ($R_3NH^+)X^-$), especially cholesteryl-3β-N-(dimethyl-aminoethyl)-carbamate or mixtures thereof, wherein $X^-$ means a counter-anion, e.g. a halogenide. Examples of suitable anionic surfactants are alkyl sulfonate (R—$SO_3M$), especially dodecyl sulfate, e.g. sodium dodecyl sulfate (SDS), lauryl sulfate or olefin sulfonate (R—$SO_3M$), especially sodium-n-dodecyl-benzene sulfonate or alkyl sulfates (R—$OSO_3M$) or fatty acids (R—COOM), especially dodecanoic acid sodium salt or phosphoric acid or cholic acids or fluoroorganics, especially lithium-3-[2-(perfluoroalkyl)ethylthio]propionate or mixtures thereof. Particularly preferred are surfactants having 1 to 30 carbons in their alkyl or olefin group.

Further, it is preferred to use a polymeric substance which provides charged groups and hydrophobic sides, in particular, poly(styrene sulfonate) (PSS) as amphiphilic substance.

Polyelectrolytes, generally, are understood as polymers having ionically dissociable groups, which can be a component or substituent of the polymer chain. Usually, the number of these ionically dissociable groups in polyelectrolytes is so large that the polymers in dissociated form (also called polyions) are water-soluble. The term polyelectrolytes is understood in this context to cover also ionomers, wherein the concentration of ionic groups is not sufficient for water-solubility, however, which have sufficient charges for undergoing self-assembly. However, the shell preferably comprises "true" polyelectrolytes, i.e. water-soluble polyelectrolytes.

Depending on the kind of dissociable groups polyelectrolytes are classified as polyacids and polybases.

When dissociated polyacids form polyanions, with protons being split off, which can be inorganic, organic and biopolymers. Examples of polyacids are polyphosphoric acid, polyvinylsulfuric acid, polyvinylsulfonic acid, polyvinylphosphonic acid and polyacrylic acid. Examples of the corresponding salts which are also called polysalts, are polyphosphate, polysulfate, polysulfonate, polyphosphonate and polyacrylate.

Polybases contain groups which are capable of accepting protons, e.g. by reaction with acids, with a salt being formed. Examples of polybases having dissociable groups within their backbone and/or side groups are polyallylamine, polyethylimine, polyvinylamine and polyvinylpyridine. By accepting protons polybases form polycations.

Suitable polyelectrolytes according to the invention are also biopolymers such as alginic acid, gummi arabicum, nucleic acids, pectins, proteins and others as well as chemically modified biopolymers such as carboxymethyl cellulose and lignin sulfonates as well as synthetic polymers such as polymethacryl acid, polyvinylsulfonic acid, polyvinylphosphonic acid and polyethylenimine.

Linear or branched polyelectrolytes can be used. Using branched polyelectrolytes leads to less compact polyelectrolyte multilayers having a higher degree of wall porosity. To increase capsule stability polyelectrolyte molecules can be crosslinked within or/and between the individual layers, e.g. by crosslinking amino groups with aldehydes. Furthermore, amphiphilic polyelectrolytes, e.g. amphiphilic block or random copolymers having partial polyelectrolyte character, can be used to reduce permeability towards polar small molecules. Such amphiphilic copolymers consist of units having different functionality, e.g. acidic or basic units, on the one hand, and hydrophobic units, on the other hand, such as styrenes, dienes or siloxanes which can be present in the polymer as blocks or distributed statistically. By using copolymers which due to outside conditions change their structure the permeability or other properties of the capsule walls can be controlled in a defined manner. In this context, for example, copolymers having a poly(N-isopropyl-acrylamide) part, e.g. poly(N-isopropylacrylamide-acrylic acid) are possible which, via the equilibrium of hydrogen bonds, change their water solubility as a function of temperature, which is accompanied by swelling.

By using polyelectrolytes which are degradable under certain conditions, e.g. photo-, acid- or base-labile, the release of enclosed active substance can be further controlled via the dissolution of the capsule walls. Further, for certain applications, conductive polyelectrolytes or polyelectrolytes having optically active groups can be used as capsule components. Basically, there are no limitations with regard to the polyelectrolytes and ionomers, respectively, to be used, as long as the molecules used have sufficiently high charge or/and are capable of binding with the layer beneath via other kinds of interaction, e.g. hydrogen bonds and/or hydrophobic interactions.

Suitable polyelectrolytes, thus, are both low-molecular polyelectrolytes and polyions, respectively, e.g. having molecular weights of a few hundred Daltons, up to macromolecular polyelectrolytes, e.g. polyelectrolytes of biological origin, having a molecular weight of several million Daltons.

Further examples of an organic polymer as bioelectrolyte are bio-degradable polymers such as polyglycolic acid (PGA), polylactic acid (PLA), polyamides, poly-2-hydroxybutyrate (PHB), polycaprolactone (PCL), poly(lactic-co-glycolic)acid (PLGA), fluorescent-labelled polymers, conducting polymers, liquid crystal polymers, photocontacting polymers, photochromic polymers and their copolymers and/or mixtures thereof.

Examples of biopolymers preferred as polyelectrolyte are polyamino acids, in particular, peptides, S-layer proteins, polycarbohydrates such as dextrin, pectin, alginate, glycogen, amylose, chitin, chondroitin, hyarulonic acid, polynucleotides, such as DNA, RNA, oligonucleotides or/and modified biopolymers such carboxymethyl cellulose, carboxymethyl dextran or lignin sulfonates. Preferred examples of inorganic polymers as polyelectrolyte are polysilanes, polysilanoles, polyphosphazenes, polysulfazenes, polysulfides and/or polyphosphates.

It is also possible to deposit charged nanoparticles or biomolecules as capsule material.

The method of the invention preferably is carried out so that excess material of the starting substances used in the individual steps are separated after each treatment step. For example, an aqueous dispersion of the template particles is formed first by adding an aqueous solution of the amphiphilic substance. After separating any excess amphiphilic molecules a first polyelectrolyte species is then added to build up the first polyelectrolyte shell. After separating any excess polyelectrolyte molecules the oppositely charged polyelectrolyte species used for building up the next layer is then added. Subsequently, oppositely charged layers of polyelectrolyte molecules are applied in turn. It is possible to select identical or different polyelectrolyte species or mixtures of polyelectrolyte species for each layer having the same charge, i.e. every second layer. Between each incubation step a purification step is carried out.

The encapsulated material prepared preferably forms a stable suspension in an aquatic phase.

An advantage of the invention lies in that the capsule thickness and permeability for the controlled release of the encapsulated material can be controlled in a predetermined manner, e.g. by the number of layers, the nature of the polyelectrolytes used, the nature of the amphiphilic substances used, the nature of the nanoparticles or biomolecules, if used, an optional additional cross-linking step and conditions of polyelectrolyte assembly.

After the desired number of polyelectrolyte layers has been applied according to the invention the now encapsulated template particles can be disintegrated, if desired, leading to the formation of hollow capsules. The invention, therefore, also encompasses a process for the preparation of hollow capsules having a polyelectrolyte shell, comprising the steps: (a) treating an uncharged solid particle material with an amphiphilic substance, (b) subsequently coating the solid material with a layer of a charged polyelectrolyte or with a multilayer comprising alternating layers of oppositely charged polyelectrolytes and (c) removing the core of uncharged solid particle material by its solubilization.

Disintegration can be effected by adding reagents which are suitable for dissolving the uncharged solid core material, e.g. an organic solvent, preferably a mild organic solvent, in which the material is soluble or an acid or alkaline solvent in which the material forms a soluble salt. The organic solvent can be used in anhydrous, pure form or as $H_2O$/solvent mixtures. Representatives of suitable organic solvents are e.g. ethanol, chloroform etc. According to the invention dissolution of the template particles can be effected in a gentle manner during a short incubation period, e.g. 1 min to 1 h at room temperature. The templates disintegrate almost completely, as no residues of the particles can be detected any longer even when inspecting the remaining shells by an electron microscope.

Preferably, the hollow capsules are redispersed in an aqueous solvent or in an organic solvent. Inside the capsules there is then preferably pure solvent.

Another subject matter of the present invention are polyelectrolyte capsules obtainable by the method of the invention. In one embodiment, these capsules contain a core of uncharged solid material which served as template. The structure of such capsules thus, viewed from inside to outside, consists of the following layers: active substance, amphiphilic substance and one or more layers of polyelectrolyte. In another embodiment, the polyelectrolyte capsules have no detectable residues of the uncharged solid core material any longer, i.e. they are without core. Such hollow polyelectrolyte capsule has the following structure: hollow space, amphiphilic substance, one or more layers of polyelectrolyte. The advantage of the amphiphilic material contained in the polyelectrolyte capsules is that porosity can be controlled and determined thereby. Furthermore, by using the amphiphilic substance an even covering of the core material is achieved so that the polyelectrolyte capsules preferably have an outer shape determined by the core. It is especially preferred that the polyelectrolyte capsules according to the invention contain an active substance, especially a pharmaceutically active substance. The encapsulated active substance thereby can be identical to the encapsulated uncharged solid particle material, however, it may also have been introduced into the empty polyelectrolyte shells later on.

The capsules according to the invention preferably have a diameter in the range of from 10 nm to 50 µm, preferably from 50 nm to 10 µm. By suitable selection of the templates capsule compositions can be obtained having high monodispersity, i.e. compositions, wherein the amount of capsules, the deviation of which from the mean diameter is >50%, is less than 10% and preferably less than 1%. The capsules according to the invention also can be dried, in particular, freeze-dried and then redispersed in suitable solvents again.

It was surprisingly found that the type of amphiphile used to pre-charge the solid material, in particular, microcrystals, determined the porosity of the resulting capsules. Thus, it is possible to provide unique, highly flexible systems with tailored release properties for encapsulated substances, in particular, for drug delivery applications. For influencing porosity it is also possible to store amphiphilic substances, in particular, phospholipids, ionic surfactants or amphiphilic polyelectrolytes between the polyelectrolyte shells.

The capsules prepared by the method of the invention can be used for encapsulating active substance. These active substances can be both inorganic and organic substances. Examples of such active substances are catalysts, in particular, enyzmes, pharmaceutically active substances, polymers, colorants such as fluorescent compounds, sensor molecules, i.e. molecules reacting detectably to the change of ambient conditions such as temperature or pH, plant protection agents and aromatics. The active substances thereby can form the encapsulated uncharged solid materials themselves, or be introduced subsequently into the hollow polyelectrolyte shells obtained by dissolving the core under mild conditions, e.g. by means of an organic solvent.

The capsules also can be used as reaction chambers, especially as microreaction chambers, for chemical reactions. Due to the fact that the permeability of the capsule walls is controllable so as to let pass, for example, low-molecular substances, however, largely retain macromolecular molecules, high-molecular products forming in a reaction, e.g. polymers forming upon polymerization, can be retained easily in the interior during synthesis.

The capsules also can be used in a variety of other applications, e.g. in sensorics, surface analytics, pharmacy, medicine, food technology, biotechnology, cosmetics, information technology and printing industry (e.g. encapsulation of coloring materials).

In the following the invention is explained in detail by the two model substances: pyrene (PYR) and fluoresceine diacetate (FDA), however, it can also be carried out in general with other uncharged solid materials.

Pyrene (PYR) and fluorescein diacetate (FDA) were employed as the uncharged microcrystalline templates. Both PYR and FDA have a very low solubility in water. The first and significant step in the encapsulation involved imparting a charge on the crystal surface by self-assembly of an amphiphilic substance, in particular a ionic surfactant, a phospholipid or polyelectrolyte having an amphiphilic nature such as charged polymer that is amphipatic. Preferably, the micrometer-sized crystals were dispersed in water, e.g. by sonicating them in the presence of ionic surfactant.[20] The amphiphilic film stabilizes the microcrystal by both hydrophobic and hydrophilic interactions, coating and enveloping it and thus protecting it from aggregation. The stable and charged microcrystals coated with the amphiphilic substance, in particular, a charged surfactant, were then exposed to polyelectrolyte (bearing an opposite charge to the amphiphilic substance adsorbed on the crystalline template), resulting in their additional coating with a polymer layer. Subsequent consecutive adsorption of oppositely charged polyelectrolytes resulted in the formation of polymer multilayers on the microcrystal colloidal core.[21]

Thus, the assembly of polymer multilayers onto the coated microcrystal templates can be achieved by a layer-by-layer adsorption of cationic and anionic polyelectrolytes.

Figure 2:
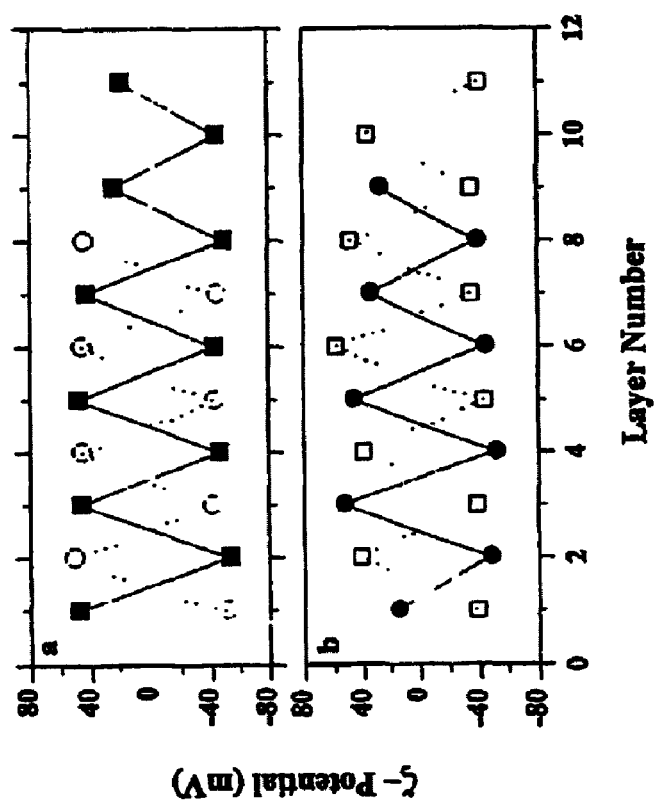

FIG. 2 shows the $\zeta$-potential as a function of the polymer coating layer number for PYR and FDA microcrystals pre-exposed to surfactant (DDDAB or SDS, FIG. 2a), DPPC or PSS (FIG. 2b). PYR crystals exposed to DDDAB (positively charged) showed a $\zeta$-potential of +50 mV, while SDS (negatively charged) dispersed FDA crystals exhibited a value of −50 mV. Furthermore, FDA microcrystals dispersed with DPPC yielded a $\zeta$-potential of +20 mV and those exposed to PSS a value of −40 mV. These data confirm charging of the microcrystal surface through adsorption of the amphiphilic substances or PSS, explaining the dispersability of the microcrystals in aqueous solution. The adsorbed layer coats the microcrystal, thus protecting it from aggregation.

The mechanism of microcrystal dispersion and stabilization can be explained by the hydrophobic interactions between the amphiphiles and the microcrystals. Since both PYR and FDA are hydrophobic, the hydrophobic chains of the surfactants and those on DPPC are expected to be associated with the microcrystal surface, while the ionic groups on these amphiphiles project away from the surface.[26] It is worthy to note that neither the PYR nor FDA microcrystals could be readily dispersed with the polyelectrolytes PAH, poly(diallyldimethylammonium chloride) (PDADMAC), or copolymers of DADMAC and acrylamide with varying DADMAC contents (8–73 mol %). In contrast, the microcrystals could be dispersed by exposure to PSS. The amphiphilic nature of PSS, owing to the aromatic group on the polymer backbone (and the charged groups), may be responsible for the successful adsorption and consequent charging of the crystal surface. The coated microcrystals are prevented from further growth (i.e. aggregation) by the ionic and/or steric interactions of the thin coating that is tightly associated with each microcrystal particle. These surface modified microcrystals represent stable and charged colloids suitable for polyelectrolyte multilayer coating.

As depicted in FIG. 2, an alternating sign in the $\zeta$-potential was observed when the pre-charged crystals were exposed to polymer solutions of opposite charge. The sign of the $\zeta$-potential depended on the polyelectrolyte that formed the outermost layer, i.e. the polymer that was deposited. Regardless of the microcrystal type (PYR or FDA), or the amphiphile used to coat and stabilize the microcrystals, alternating positive and negative $\zeta$-potentials were measured for coated crystals alternately exposed to PAH and PSS, respectively. This shows that step-wise growth of the polymers on the microcrystal template occurred, and is characteristic of polymer multilayer formation on charged colloidal particles. Values of ca. +50 mV were observed when PAH formed the outermost layer and −50 mV when PSS was deposited last. The slightly lower positive values observed for the PAH-FITC (FITC: fluorescein isothiocyanate) layers (ca. +20 mV) is attributed to the high loading of negatively charged FITC molecules on the PAH chains. Importantly, the amphiphiles were strongly adsorbed onto the microcrystals allowing the formation of polymer multilayers.

According to the invention, charged surfactants, lipids or amphiphilic polymers can be used to charge hydrophobic crystalline templates, thus facilitating their encapsulation with polyelectrolyte multilayers. Surprisingly, the amphiphilic substances are not removed from the surfaces of the uncharged solid material when a polyelectrolyte is added, but serve as linkers for the attachment of the polyelectrolyte onto the uncharged solid material.

Additional evidence for the successful encapsulation of the uncharged microcrystals was obtained by transmission and fluorescence confocal laser scanning microscopy (CLSM) measurements. CLSM was employed to investigate the morphology of the microcrystals and to verify their coating with polymer multilayers. A fluorescently labelled polyelectrolyte (FITC-PAH) was adsorbed as the outermost layer on the pre-coated microcrystal colloids in order to allow its visualisation by fluorescence microscopy. The regular coverage of FITC-PAH on the crystal surface was confirmed by fluorescence microscopy, whilst the transmission micrographs showed that the coated microcrystal consisted of a solid core. The coated microcrystals could be stored for days without any noticeable change in morphology.

Figure 3:
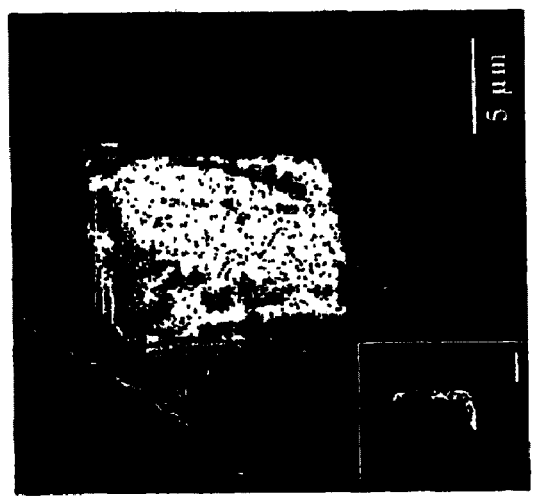

FIG. 3 displays a CLSM image (in transmission mode) of a FDA microcrystal that has been dispersed as a result of coating with PSS and additionally coated with nine polyelectrolytes layers (the last layer was PAH-FITC). The inset shows the corresponding CLSM fluorescence micrograph. It is evident from the transmission image the microcrystal possesses a solid core. The microcrystals had various shapes, ranging from near-spherical to rod-like, square and rectangular. Direct evidence for polymer coating of FDA is provided in the CLSM fluorescence image (inset). This displays fluorescence due to PAH-FITC present in the outer layer of a coated microcrystal. Similar CLSM images were observed for pre-dispersed FDA and PYR crystals coated with polymer. Studies showed that the coated microcrystal suspensions were stable for days when stored in an aqueous medium, reflecting the stability of the adsorbed layers.

Direct proof that a polymer multilayer cage encapsulated the microcrystals was obtained by removing the templated core. The release behaviour of the pyrene and fluoresceine diacetate molecules, from dissolution of the core templates, through the polymer capsule wall can be investigated by using fluorescence spectroscopy. Following centrifugation of the coated microcrystal suspensions that were exposed to ethanol, the supernatant was assessed for either pyrene or fluoresceine at regular time intervals.

Control experiments for DDDAB-dispersed PYR microcrystals and those dispersed with PSS revealed rapid release characteristics: Upon addition of ethanol, the pyrene core was removed within about 30 min for both the surfactant- and PSS-coated crystals. The pores in the polymer microcapsules produced in this work are large enough to allow removal of the low molecular weight core molecules (see below). This finding is consistent with earlier reports on the permeability characteristics of polyelectrolyte multilayers: Polymer multilayers are permeable to low molecular weight substances[14,15] but essentially impermeable to polymers larger than 4000 Da.[27] Further experiments showed that the rate of removal was found to be dependent on the first layer adsorbed, the number of polyelectrolyte layers, and the ratio of ethanol to water in the dissolving medium. It is worth noting that up to five polyelectrolyte layer pairs were assembled onto the microcrystal templates in the current work. Slower release rates were observed with increasing polyelectrolyte layer number. The assembly of thicker shells (e.g. more polyelectrolyte layers) may have the effect of smoothing out the outer surface and at the same time reducing the porosity. The layer-by-layer assembly of polycations and polyanions displays a remarkable self-regularity: For films grown on poorly charged and/or rough planar substrates, irregular growth has often been observed for the first few layers with regular growth achieved after the deposition of a number of layer pairs.[30-32]

Figure 4:
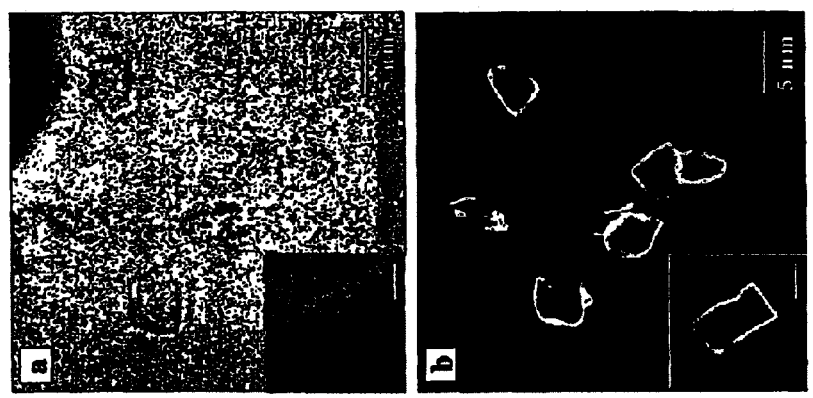

The CLSM micrographs of polymer-coated FDA microcrystals after being exposed to ethanol solution and dispersed in water are displayed in FIG. 4. The transmission image (a) shows a number of the hollow colloidal entities produced. There is no evidence of a solid core, indicating dissolution and removal of the microcrystal. Ethanol solubilizes the core material and the individual molecules are then able to diffuse through the semi-permeable polymer capsule walls. The structures seen in the transmission image are due to the contrast of the remaining polymer layers from the original coating of the microcrystals, indicating the successful formation of hollow polymer capsules. The above results are consistent with the visual observation that the polymer-coated microcrystal suspensions lost their turbidity upon the addition of ethanol. Further evidence is provided by the corresponding CLSM fluorescence image (b), which shows the fluorescence from the PAH-FITC layers. The different morphologies observed are due to the diversity of the microcrystal shapes. Some indentations on the polymer capsule walls may also be due to the centrifugation process used in their preparation. There was no evidence of rupturing of the capsule walls as a result of the facile removal of the microcrystal core by treatment with ethanol. The CLSM results demonstrate that polymer multilayers can be deposited onto pre-charged microcrystal templates and that the core can be removed by treatment with an appropriate solvent, leaving behind hollow polymer capsules.

Figure 5:
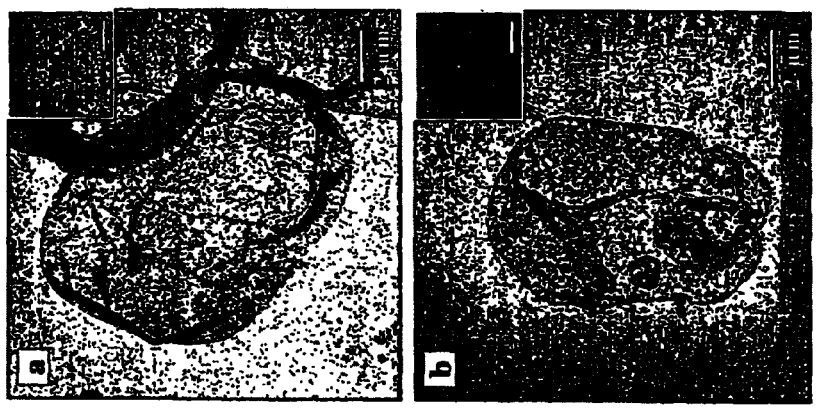

The polyelectrolyte capsules produced were further characterized using TEM and AFM. TEM images of air-dried hollow polymer capsules obtained from SDS-dispersed PYR microcrystals coated with eleven polymer layers, and FDA crystals dispersed with PSS and additionally coated with nine polyelectrolyte layers, are illustrated in FIGS. 5 (a and b, respectively). The insets are higher magnifications. The folds and creases seen in the polymer capsules are a result of evaporation of the aqueous content by air-drying.[10] The striking difference between FIG. 5a and FIG. 5b is the wall porosity. Capsules produced when the microcrystals were dispered with surfactant (either positively or negatively charged) exhibit a much smoother texture and lower porosity than those produced from PSS-dispersed microcrystals. Pores of diameter from 20 nm to larger than 100 nm were observed for hollow capsules derived from polymer-coated PSS-dispersed microcrystals. In contrast, it was difficult to discern pores in the very smooth textured polymer capsules when surfactant was used to disperse the microcrystals, suggesting an average pore size of less than about 5–10 nm. These findings were confirmed by AFM measurements. The differences seen may be ascribed to the initial conformation of the first adsorbed layer (in terms of homogeneity) used to disperse the crystals. Nevertheless, the above illustrates the importance of the first adsorbed layer in determining the porosity of the resulting thin-walled hollow polymer capsules. Control over the pore size in such hollow microcapsules is expected to have important implications in technology as it allows regulation of the release rate of encapsulated materials.

Examination of the apparent heights of air-dried polymer capsules by using tapping mode AFM yielded values of approximately 25–30 nm for capsules comprised of 10 polyelectrolyte layers. This dimension is equivalent to twice the polymer capsule wall thickness; hence, the average thickness per polyelectrolyte layer is between 1 to 1.5 nm, a value that is close to those obtained for polymer multilayers on other colloidal templates.[10]

An attractive feature of the process employed for the formation of hollow polymer capsules is the facile removal of the templated microcrystal core. Previous methods have involved extremely acidic (pH=1)[10,15] or basic (>12)[10,17] solutions. Clearly the use of such conditions is limited, particularly when biological compounds are present during the core removal process. In addition, the undesirable changes in the composition and properties of the hollow polymer capsules that occur with such harsh conditions[29] can be avoided.

In summary, the colloid-template approach based on uncharged organic microcrystals complements other strategies we have been developing for encapsulating various materials. This method is of particular relevance and importance because of its potential to encapsulate a wide range of uncharged crystalline drugs. In addition, its versatility and the control that it permits over the polymer multilayer wall thickness and composition allows for the creation of a drug release system with a tailored release rate. The systems prepared provide excellent model drug release systems to study various parameters on the release rate of encapsuled low molecular weight compounds. An interesting strategy is to control the release rate by varying the thickness and composition of the polymer capsule walls.

The invention is further illustrated by the following examples and figures.

FIG. 1 is a schematic representation of a preferred embodiment of the process used to encapsulate organic microcrystals and to create hollow polymer cages. The uncharged microcrystals are coated by the self-assembly of charged surfactant molecules (step 1), rendering them water dispersible and hence amenable to subsequent coating with polyelectrolyte multilayers (step 2). Each polyelectrolyte layer deposited has an opposite charge to that already adsorbed. Hollow polymer multilayer cages are formed by direct exposure of the encapsulated microcrystals to ethanol, causing their solubilisation and removal (step 3). Some surfactant may be electrostatically bound to the hollow polymer cages.

Step 1 of FIG. 1 can, of course, be varied, e.g. by use of a polyelectrolyte (e.g. PSS) or phospholipids to coat and pre-charge the microcrystals.

FIG. 2 shows the $\zeta$-potential of amphiphile-stabilised PYR and FDA microcrystals as a function of polyelectrolyte layer number: (a) PYR-DDDAB (filled squared), FDA-SDS (open circles); (b) FDA-DPPC (filled circles); FDA-PSS (open squares). Layer number=1 corresponds to the amphiphile-coated microcrystals. Surface charge reversal is seen with adsorption of each polyelectrolyte layer. From layer number 2 onwards, positive values are for PAH adsorption and negative values for PSS deposition. Layer 9 and 11 for the PYR-DDDAB system and layer 10 for the FDA-PSS system correspond to PAH-FITC adsorption.

FIG. 3 shows the transmission and fluorescence (inset) CLSM micrographs of an FDA crystal dispersed by adsorption of PSS and further coated with nine polyelectrolyte layers, with the outermost layer being PAH-FITC, [(PAH/PSS)$_4$/PAH-FITC].

FIG. 4 shows the CLSM transmission (a) and fluorescence (b) micographs of hollow polymer capsules derived from polymer-coated FDA microcrystals. The polymer cages were obtained from polymer-coated FDA microcrystals. The FDA microcrystals were dispersed by adsorption of PSS and additionally coated with nine polyelectrolyte layers with the outermost layer being PAH-FITC, [(PAH/PSS)$_4$/PAH-FITC]. The insets show an individual hollow polymer cage, obtained after dissolution of the core from FDA dispersed with SDS and coated with eleven polyelectrolyte layers [(PAH/PSS)$_4$/PAH-FITC]. The scale bars in the insets correspond to 2 µm.

FIG. 5 shows the TEM images of air-dried hollow polymer capsules, obtained after removal of the templated microcrystal core with ethanol. (a) The PYR core was dispersed by SDS and coated with eleven polyelectrolyte layers. (b) FDA was dispersed by PSS and coated with nine polyelectrolyte layers. The polymer capsules flattened as a result of drying and folds and creases are seen. A significant difference in porosity was observed for the polymer capsules, depending on whether surfactant (a, less porous) or PSS (b, more porous) was used to disperse the microcrystals. Similar differences were observed for both the PYR and FDA systems. The scale bars in the insets correspond to 200 nm.

EXAMPLES

1. Materials

Pyrene (PYR) was purchased from Aldrich and fluorescein diacetate (FDA) from Sigma. The polycation, poly (allylamine hydrochloride) (PAH), $M_w$ 15,000, and the polyanion, poly(sodium 4-styrenesulfonate) (PSS), $M_w$ 70,000, were obtained from Aldrich. The positively charged surfactants didodecyldimethylammonium bromide (DDDAB), hexadecyltrimethylammonium bromide (HDTAB), dodecyltrimethylammonium bromide (DTMAB), myristyltrimethylammonium bromide (MTMAB), and the negatively charged surfactant sodium dodecylsulfate (SDS) were all from Aldrich. Dipalmitoyl-DL-α-phosphatidylcholine (DPPC) was purchased from Sigma. All reagents were used as received, except for the PSS, which was dialyzed against Milli-Q water ($M_w$ cut-off 14,000) and lyophilized before use.

2. Preparation of Fluorescein Isothiocyanate Labeled PAH (PAH-FITC):

An aqueous solution of 500 mg PAH in 6 ml water is adjusted to a pH of 8.1 with 1 M NaOH. An aqueous solution of 4 mg FITC in 500 µl DMSO is added to the PAH solution (conjugation ratio FITC/PAH-monomer is 1/500). The mixture is incubated overnight at room temperature and then filtrated with a 3 µm filter. The unconjugated FITC is removed from the conjugate by gel filtration over a PD-10 column (Pharmacia). The final fractions are dialysed against deionised water overnight by using a 0.5–2 ml Slide-A-Lizer frame (Pierce) with a cut-off of molecular weight of 3500 dalton. Yield: 25 ml PAH-FITC solution with a concentration of 9 mg/ml.

3. Assembly of Polyelectrolyte Multilayers onto Organic Microcrystals

The layer-by-layer assembly of polyelectrolytes onto FDA or PYR microcrystals was carried out as follows: 50 mg of finely milled core particles (FDA or PYR) were first thoroughly mixed with 12 mL of 0.2–0.4 wt % of the dispersing agent (ionic surfactant, lipid or charged polymer). Crystalline fluorescein diacetate or pyrene can be milled to fine particles using e.g. a mortar and pestle. However, also advanced ball milling procedures can be used.

The crystals were suspended by their immediate sonication for 5 min. The suspension was allowed to stand for 30 min, thus allowing the larger crystals to sediment, or gently centrifuged. The turbid white supernatant was then extracted, centrifuged and washed several times, and finally resuspended in water.

The resulting microcrystal particles were then layer-by-layer coated with PSS and PAH.[18] When positively charged surfactants or DPPC were used as the first layer, 1 mL of PSS solution (5 mg mL$^{-1}$, containing 0.5 M NaCl) was added first. PAH solution (1 mL of 5 mg mL$^{-1}$, containing 0.5 M NaCl) was added first when PSS or SDS were adsorbed onto the microcrystals. After an adsorption time of 15 min for PAH or PSS adsorption, the suspension was centrifuged at 3000 g for 5 min. The supernatant was then removed and three cycles of water washing and redispersing were applied to remove the excess unadsorbed polyelectrolyte in solution. Subsequent polyelectrolyte layers, bearing an opposite charge to that already adsorbed on the particle, were deposited in identical fashion to produce multilayer-coated microcrystals. In some cases, the fluorescently labeled polyelectrolyte, PAH-FITC, was applied (as a 2 mg mL$^{-1}$ solution containing 0.5 M NaCl) to form a fluorescent layer on the microcrystal surface.

The order of polyelectrolyte coating and the resulting zeta-potentials are given in Tables 1 and 2 and are also graphically shown in FIG. 2.

TABLE 1

Zeta-potential of fluorescein diacetate crystals as a function of the layer number and polyelectrolyte
Template: Fluorescein diacetate

| Layer No. | Coating | Zeta-potential |
| --- | --- | --- |
| 1 | SDS detergent | −850 mV |
| 2 | PAH | +42.9 mV |
| 3 | PSS | −37.7 mV |
| 4 | PAH | +51.5 mV |
| 5 | PSS | −42.2 mV |
| 6 | PAH-FTTC | +48.2 mV |

TABLE 2

Zeta-potential of pyrene crystals in as a function of the layer number and polyelectrolyte
Template: Pyrene

| Layer No. | Coating | Zeta-potential |
| --- | --- | --- |
| 1 | SDS detergent | −68.5 mV |
| 2 | PAH | +59 mV |

TABLE 2-continued

Zeta-potential of pyrene crystals in as a function of the layer number and polyelectrolyte
Template: Pyrene

| Layer No. | Coating | Zeta-potential |
|---|---|---|
| 3 | PSS | −46.5 mV |
| 4 | PAH | +54.3 mV |
| 5 | PSS | −37.2 mV |
| 6 | PAH-FTTC | +47.3 mV |

The treatment of the crystals with the SDS solution leads to a high negative surface charge (see layer No. 1 in Tables 1 and 2). The resulting suspensions are highly stable and ideally suitable as templates for the coating with polyelectrolytes. The alternating charge of the zeta-potential indicates the successful coating. The coating was also confirmed by the application of FITC conjugated PAH, and its visualisation by fluorescent microscopy.

The morphology of the crystals is not changed during the coating procedures. The yield of coated substance is only decreased by a small loss in the centrifugation/washing step, and can be optimised to high rates, around 98%.

In addition to the previously described experiment, encapsulations under different conditions (surfactant concentration 0.2–0.4 wt %, sonication 5–30 min., lower polyelectrolyte concentrations) were also carried out successfully.

4. Release Experiments 12 mL of solvent (ethanol or ethanol/water mixtures) were dispensed into 15 mL tubes. 0.1 mL of the coated microcrystal suspension of Example 3 was then quickly added to each tube and after defined times (2, 5, 10 min etc.) the suspension was centrifuged at 3000 g for 5 min. A portion of the supernatant was removed and tested for the presence of PYR of FDA by fluorescence. For PYR, the fluorescence emission intensity of the supernatant was measured directly by using an excitation wavelength ($\lambda_{ex}$) of 350 nm and monitoring the emission ($\lambda_{em}$) at 373 nm. FDA was first hydrolyzed into fluorescein either by treatment with esterase or dilute base prior to fluorescence measurement ($\lambda_{ex}$=492 nm, $\lambda_{em}$=513 nm). As control experiments, the release characteristics of uncoated particles was also studied as outlined above.

5. Production of Hollow Polymer Capsules by Removing of the Hydrophobic Template with Organic Solvents The microcrystal core was removed by exposing 0.2 mL of the coated particle suspension of Example 3 to 1 mL of ethanol (or chloroform) and allowing 30 min for core dissolution. The resulting hollow polymer capsules were then centrifuged at 10000 g for 10 min, exposed to ethanol again, washed a further two times with water, and finally resuspended in water.

The resuspended shells were analysed by confocal fluorescence microscopy demonstrating that hollow shells are obtained by the method. The shape of the shells is irregular due to initial shape of the template. This can be optimized or tailored by suitable choice of the template.

6. Instruments and Test Methods

Microelectrophoresis

The microelectrophoretic mobility of coated organic microcrystals was measured with a malvern Zetasizer 4 by taking the average of 5 measurements at the stationary level. The mobilities ($\mu$) were converted to the electrophoretic potentials ($\zeta$) using the Smoluchowski relation $\zeta=\mu\eta/\epsilon$, where $\eta$ and $\epsilon$ are the viscosity and permittivity of the solution, respectively.[25] All measurements were performed on microcrystals re-dispersed in air-equilibrated pure water (pH ~5.6).

Confocal Laser Scanning Microscopy (CLSM)

CLSM images were taken on a confocal laser scanning Aristoplan microscope from Leica with a 40×oil immersion objective.

Transmission Electron Microscopy (TEM)

TEM measurements were performed on a Philips CM12 microscope operating at 120 kV. TEM samples were prepared by deposition of a diluted particle suspension onto a carbon-coated copper grid. The mixture was allowed to air dry for one minute, after which the time exces solution was removed by blotting with filtered paper.

Atomic Force Microscopy (AFM)

AFM images were obtained using a Nanoscope IIIa AFM (Digital Instruments, CA) in tapping mode. Samples were prepared by applying a drop of a diluted solution onto a freshly cleaved mica surface, allowing 1 min for air drying, and then blotting off the extra solution.

Fluorescence Spectroscopy

Steady state fluorescence spectra were recorded using a Spex Fluorolog 1680 spectrometer. Both excitation and emission bandwidths were set at 1.0 nm. All measurements were performed on air-equilibrated solutions at 25° C.

REFERENCES AND NOTES

1. Park, K. *Controlled Drug Delivery: Challenges and Strategies*, Am. Chem. Soc., Washington D.C., 1997
2. Ribeiro, A. J.; Neufeld, R. J.; Arnaud, P.; Chaumeil, J. C. *Int. J. Pharm.* 1999, 187, 115
3. Langer, R. *Nature* 1998, 392, 5–10
4. Rilling, P.; Walter, T.; Pommersheim, R.; Vogt, W. *J. Membrane Sci.* 1997, 129, 283.
5. Hari, P. R.; Chandy, T.; Sharma, C. P. *J. Microencapsulation* 1996, 13, 319.
6. Kreuter, J. *Colloidal Drug Delivery Systems*, Marcel Dekker, New York, 1994.
7. Arshady, R. *J. Controlled Release* 1991, 17, 1.
8. Kirpotin, D.; Chan, D. C. F.; Bunn, P. WO 98/14180, 1998.
9. Haynes, D. H. U.S. Pat. No. 5,091,187, 1992.,
10. For a review, see: Caruso, F. *Chem. Eur. J.* 2000, 6, 413.
11. Caruso, F.; Möhwald, H. *Langmuir* 1999, 15, 8276.
12. Caruso, F.; Caruso, R. A.; Möhwald, H. *Chem. Mater.* 1999, 11, 3309.
13. Caruso, F.; Caruso, R. A., Möhwald, H. *Science* 1998, 282, 1111.
14. Caruso, F.; Donath, E.; Möhwald, H. *J. Phys. Chem. B* 1998, 102, 2011.
15. Donath, E.; Sukhorukov, G. B.; Caruso, F.; Davis, S. A.; Möhwald, H. *Angew. Chem. Int. Ed.* 1998, 37, 2201.
16. Caruso, F.; Möhwald, H. *J. Am. Chem. Soc.* 1999, 121, 6039.
17. Caruso, C. Schuler and D. G. Kurth, *Chem. Mater.,* 1999, 11, 3394.
18. Caruso, F.; Trau, D.; Möhwald, H.; Renneberg, R. *Langmuir* 2000, 16, 1485.
19. D. H. Haynes, U.S. Pat. No. 5,091,187, 1992.
20. 50 mg of finely milled crystalline core (PYR or FDA, Aldrich) was added to 12 mL of a 0.2 wt % surfactant (SDS or DDDAB, Aldrich) aqueous solution. The crystals were suspended by their immediate sonication for 5 min. The suspension was allowed to stand for 30 min, thus allowing the larger crystals to sediment. The turbid white supernatant was then extracted, centrifuged and washed several times, and finally resuspended in water.

21. PAH/PSS multilayers were prepared on the templates using the procedure previously described.[5] Briefly, the surfactant-coated microcrystals were exposed to 1 mL of a 5 mg mL$^{-1}$ polyelectrolyte solution (either PSS, $M_w$ 70,000, or PAH, $M_w$ 15,000 (Aldrich), depending on the surfactant used) containing 0.5 M NaCl. After a 15 min adsorption time, the excess polyelectrolyte was removed by repeated centrifugation and wash cycles. Subsequent polyelectrolyte layers were deposited in identical fashion.

22. F. Caruso, H. Lichtenfeld, E. Donath and H. Möhwald, *Macromolecules*, 1999, 32, 2317.

23. D. Myers, *Surfactant Science and Technology*, Second Edition, VCH, Weinheim, 1992.

24. The microcrystals could not be readily dispersed by simply exposing them to polyelectrolyte (e.g. PAH, poly (diallyldimethylammonium chloride) (PDADMAC) and copolymers of DADMAC and acrylamide). The only exception was PSS, which contains an aromatic group that is possibly responsible for its amphiphilic behaviour in coating the microcrystals and stabilising them.

25. Hunter, R. J. *Foundations of Colloid Science*, Clarendon Press, Oxford, 1989, Vol. 11, p. 807.

26. Myers, D. *Surfactant Science and Technology*, Second Edition, VCH, Weinheim, 1992.

27. Sukhorukov, G. B.; Brumen, M.; Donath, E.; Möhwald, H. *J. Phys. Chem. B* 1999, 103, 6434.

28. Moya, S.; Sukhorukov, G. B.; Auch, M.; Donath, E.; Möhwald, H. *J. Colloid Interface Sci.* 1999, 216, 297.

29. Moya, S.; Dähne, L.; Voigt, A.; Donath, E.; Möhwald, H. Submitted for publication.

30. Decher, G.; Schmitt, J. *Prog. Colloid Polym. Sci.* 1992, 89, 160.

31. Lvov, Y.; Decher, G.; Möhwald, H. *Langmuir* 1993, 9, 481.

32. Caruso, F.; Niikura, K., Furlong, D. N.; Okahata, Y. *Langmuir* 1997, 13, 3422.

The invention claimed is:

1. A process for the encapsulation of an uncharged crystalline solid particle material comprising:
   (a) treating the crystalline solid particle material with an amphiphilic substance and
   (b) subsequently coating the material with a layer of a charged polyelectrolyte or with a multilayer comprising alternating layers of oppositely charged polyelectrolytes.

2. The process according to claim 1, wherein the solid material has a low solubility in water, is water insoluble or not water-dispersible.

3. The process of claim 1, wherein the solid material is an organic material, a bio-material or an inorganic material.

4. The process according to claim 1, wherein the solid material is selected from the group consisting of drugs, vitamins, nutrients, hormones, growth factors, pesticides, antibiotics and preservatives or mixtures thereof.

5. The process according to claim 1, where the solid material is selected from the group consisting of single crystals.

6. The process according to claim 1, wherein the solid material is a synthetic material or a material isolated from natural sources or a chemical modified isolated material.

7. The process according to claim 1, wherein the amphiphilic substance is selected from ionic surfactants, phospholipids and amphiphilic polyelectrolytes.

8. The process according to claim 1, wherein a cationic or an anionic surfactant or a combination of anionic and cationic surfactants is used.

9. The process according to claim 8, wherein the cationic surfactant is selected from the group consisting of quarternary ammonium salts (($R_4N^+$)$X^-$), alkyltrimethylamoniumbromides, N-alkyl pyridinium salts, tertiary amines, (($R_3NH^+$)$X^-$), secondary amines (($R_2NH_2^+$)$X^-$), primary amines (($RNH_3^+$)$X^-$) and mixtures thereof.

10. The process according to claim 8, where the anionic surfactant is selected from the group consisting of alkylsulfonates (R—$SO_3$M), olefinsulfonates (R—$SO_3$M), alkylsulfates R—$OSO_3$M, fatty acids (R—COOM), phosphoric acids, cholic acids, fluoro organics, and mixtures thereof.

11. The process according to claim 8, wherein the amphiphilic substance is selected from the group consisting of a polymeric substance which provides charged groups and hydrophobic sides, and block-copolymers.

12. The process according to claim 1, wherein the polyelectrolyte is selected from the group consisting of organic polymers, bio-polymers, inorganic polymers and mixtures thereof.

13. The process according to claim 1, wherein the polyelectrolyte is a linear or a non-linear polymer or mixtures thereof.

14. The process according to claim 1, wherein the polyelectrolyte is a block-copolymer.

15. The process according to claim 1, wherein the polyelectrolyte is cross-linked after templating.

16. The process according to claim 15, wherein the cross-linking is provided between the polymers in one layer or/and between the layers.

17. The process according to claim 12, wherein the polyelectrolyte is an organic polymer selected from the group consisting of bio-degradable polymers, fluorescent labelled polymers, conducting polymers, liquid crystal polymers, photo conducting polymers, photochromic polymers and their copolymers and mixtures thereof.

18. The process according to claim 12, wherein the polyelectrolyte is a bio-polymer selected from the group consisting of poly amino acids, poly carbohydrates, poly nucleotides, oligonucleotides and modified bio-polymers.

19. The process according to claim 12, wherein the polyelectrolyte is an inorganic polymer selected from group consisting of polysilanoles, polysilanoles, polyphosphazenes, polysulfazenes, polysulfides, polyphosphates and mixtures thereof.

20. The process according to claim 1, wherein charged nanoparticles and/or biomolecules are deposited as capsule materials.

21. The process according to claim 1, wherein excessive material of amphiphilic substances, polyelectrolytes and/or nanoparticles and biomolecules, that are not contributed to forming the coating, are separated after each coating step.

22. The process according to claim 1, wherein the encapsulated material is forming a stable suspension in an aquatic phase.

23. The process according to claim 1, wherein the capsule thickness and permeability for the controlled release of the encapsulated material is controlled by at least one of the following features: the nature of the surfactant, the number of layers, the nature of the polyelectrolyte, the nature of the nanoparticles or biomolecules, an additional cross-linking step, the conditions of polyelectrolyte assembly and the nature of amphiphilic coating.

24. A process for the preparation of capsules having a polyelectrolyte shell, comprising the steps:
   (a) treating an unchared crystalline solid particle material with an amphiphilic substance,
   (b) subsequently coating the crystalline solid material with a layer of a charged polyelectrolyte or with a multilayer comprising alternating layers of oppositely charged polyelectrolytes and
   (c) removing the core of uncharged crystalline solid particle material.

25. The process according to claim 23, wherein hollow capsules are produced from the encapsulated material by removal of the core material by exposure to an organic solvent in which the material is soluble or an acid or alkaline solvent in which the material is forming a soluble salt or mixtures thereof.

26. The process according to claim 24, wherein the hollow capsules are redispersed in an aqueous solvent or an organic solvent or mixtures thereof.

27. The process according to claim 24, wherein further a drug is incorporated into the capsules.

28. The process according to claim 1, wherein the size of pores within the capsule wall is controlled by the kind of amphiphilic substance used and/or the coating conditions of the amphiphilic substance.

29. Polyelectrolyte capsule, obtainable by a process according to claim 1.

30. Capsule according to claim 29, comprising a core consisting of uncharged solid material.

31. Capsule according to claim 29, comprising no detectable residue of the solid core material.

32. Capsule according to claim 29, having a final shape which is determined by the uncharged solid core material.

33. Capsule according to claim 29, comprising a drug.

34. A process for preparing a drug-containing capsule, comprising encapsulating a drug in a polyelectrolyte capsule as claimed in claim 29.

35. A process according to claim 29, wherein said polyelectrolyte capsule is a reaction chamber.

36. A process according to claim 29, wherein said polyelectrolyte capsule is applied in insensoric, surface-analytic or information technology applications.

37. A process according to claim 29, wherein said polyelectrolyte capsule is applied in pharmacy, medicine, food technology, biotechnology, cosmetics or in printing applications.

38. A process according to claim 29, wherein said polyelectrolyte capsule is a slow, targeted, or controlled release systems.

39. Composition containing capsules according to claim 29 in dried form.

40. Composition comprising capsules according to claim 29 having a monodisperse size distribution.

41. The process according to claim 9, wherein said quaternary ammonium salt is didodecyldimethylammonium bromide (DDDAB).

42. The process according to claim 9, wherein said alkyltrimethyl ammoniumbromide is dodecyltrimethylammonium bromide or palmithyltrimethylammonium bromide.

43. The process according to claim 9, wherein said tertiary amine is cholesteryl-3-β-N-(dimethyl-aminoethyl) carbamate.

44. The process according to claim 10, wherein said alkylsulfonate is dodecylsulfate or laurylsulfate.

45. The process according to claim 10, wherein said olefinsulfonate (R—$SO_3$M) is sodium n-dodecylbenzensulfonate.

46. The process according to claim 10, wherein said fatty acid (R—COOH) is dodecanoic acid sodium salt.

47. The process according to claim 10, wherein said fluoro organic is lithium 3-propionate.

48. The process according to claim 11, wherein said polymeric substance is poly(styrenesulfonate) (PSS).

49. The process according to claim 11, wherein said block-copolymer is poly(ethylethylene-block-styrene sulfoic acid (PEE-PSS).

50. The process according to claim 17, wherein said biodegradable polymer is polyglycolic acid (PGA), polyactic acid (PLA), polyamide, poly-2-hydroxy butyrate (PHB), polycaprolactone (PCL), or poly (lactic-co-glycolic) acid (PLGA).

51. The process according to claim 18, wherein said polyamino acid is a peptide or a S-layer protein.

52. The process according to claim 18, wherein said polycarbohydrate is dextrin, pectin, alginate, glycogen, amylose, chitin, chondroitin, or hyarulonic acid.

53. The process according to claim 18, wherein said polynucleotide is DNA or RNA.

54. The process according to claim 18, wherein said modified bio-polymer is carboxymethyl cellulose, carboxymethyl dextran, or lignin sulfonate.

* * * * *